US010835591B2

(12) United States Patent
Amin et al.

(10) Patent No.: US 10,835,591 B2
(45) Date of Patent: Nov. 17, 2020

(54) VACCINE CANDIDATE FOR PERIODONTITIS

(71) Applicants: Mohsen Amin, Tehran (IR); Saba Hashemi, Karaj (IR)

(72) Inventors: Mohsen Amin, Tehran (IR); Saba Hashemi, Karaj (IR)

( * ) Notice: Subject to any disclaimer, the term of this patent is extended or adjusted under 35 U.S.C. 154(b) by 0 days.

(21) Appl. No.: 16/718,394

(22) Filed: Dec. 18, 2019

(65) Prior Publication Data

US 2020/0108134 A1     Apr. 9, 2020

Related U.S. Application Data

(60) Provisional application No. 62/787,396, filed on Jan. 2, 2019.

(51) Int. Cl.
| | |
|---|---|
| *A61K 39/39* | (2006.01) |
| *A61K 39/02* | (2006.01) |
| *A61K 39/00* | (2006.01) |

(52) U.S. Cl.
CPC ........... *A61K 39/0225* (2013.01); *A61K 39/39* (2013.01); *A61K 2039/53* (2013.01); *A61K 2039/55566* (2013.01)

(58) Field of Classification Search
CPC ...... A61K 2039/53; A61K 2039/55566; A61K 39/0225; A61K 39/39
See application file for complete search history.

(56) References Cited

PUBLICATIONS

Journal Of Bacteriology, May 1996, vol. 178; p. 2489-2497 (Year: 1996).*

\* cited by examiner

*Primary Examiner* — Padmavathi Baskar
(74) *Attorney, Agent, or Firm* — Bajwa IP Law Firm; Haris Zaheer Bajwa

(57) ABSTRACT

A complementary DNA (cDNA) with SEQ ID NO: 1 which encodes an immunogenic fragment of major outer sheath protein (Msp) of *Treponema denticola*.

3 Claims, 5 Drawing Sheets

Specification includes a Sequence Listing.

VACCINE CANDIDATE FOR PERIODONTITIS

CROSS-REFERENCE TO RELATED APPLICATION

This application claims the benefit of priority from U.S. Provisional Patent Application Ser. No. 62/787,396, filed on Jan. 2, 2019, and entitled "PERIOVAX3, A VACCINE CANDIDATE FOR PERIODONTITIS," which is incorporated herein by reference in its entirety.

TECHNICAL FIELD

The present disclosure generally relates to vaccination against *Treponema denticola*, particularly to vaccination against periodontitis using an immunogenic fragment of *Treponema denticola*, and more particularly to a complementary DNA encoding a highly immunogenic fragment of *Treponema denticola* (*T. denticola*).

BACKGROUND

Periodontitis is an inflammatory condition that destroys the supporting tissues of teeth. There is evidence of an association between periodontitis and other diseases, such as cardiovascular disease, rheumatoid arthritis, and respiratory disease. Therefore, the development of vaccine strategies to prevent the condition itself and relevant consequences is conceivable. Three bacteria including *Porphyromonas* (*P.*) *gingivalis*, *Tannerella* (*T.*) *forsythia*, and *Treponema* (*T.*) *denticola* constitute the biofilm of which *T. denticola* has been shown to be the early colonizer and the key bacterium in the initiation of the inflammation in the periodontal pocket leading to bleeding and destruction of the tissues surrounding teeth.

Also, the outer membrane of *T. denticola* exhibits antigens that contain adhesive and cytopathic properties and are associated with the pathogenesis of periodontal disease. Major outer sheath protein (Msp) is the most extensively studied protein and a virulence factor that mediates many of the cytopathic effects and adhesive properties of *T. denticola* to fibroblasts and epithelial cells. The Msp also mediates adhesion of *T. denticola* to host extracellular matrix proteins such as fibronectin and host fibroblasts.

Since the Msp protein is in the outer membrane of *T. denticola* and is partially exposed on a bacterial surface, it may be considered as the most antigenic protein in *T. denticola*. Therefore, there is a need for an immunogenic vaccine candidate against the Msp protein of *T. denticola* that effectively stimulates the immune system and triggers antibody production in vaccinated subjects.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary complementary DNA (cDNA) including SEQ ID NO: 1. In an exemplary embodiment, the exemplary cDNA may encode an immunogenic fragment of major outer sheath protein (Msp) of *Treponema denticola*. In an exemplary embodiment, the immunogenic fragment may have a molecular weight of about 9722 Daltons. In an exemplary embodiment, the immunogenic fragment may have an isoelectric point of about 9.19. In an exemplary embodiment, the exemplary cDNA may further include a nucleotide sequence of a histidine tag (His-tag).

In another general aspect, the present disclosure describes an exemplary method for vaccination against periodontitis. In an exemplary embodiment, the exemplary method may include administering a DNA vaccine to a subject. In an exemplary embodiment, the DNA vaccine may include the exemplary cDNA with SEQ ID NO: 1. In an exemplary embodiment, the DNA vaccine may further include an adjuvant. In an exemplary embodiment, the adjuvant may include Freund's adjuvant. In an exemplary embodiment, the DNA vaccine may further include a pharmaceutically acceptable carrier.

In an exemplary embodiment, the exemplary method may include administering a peptide vaccine to a subject. In an exemplary embodiment, the peptide vaccine may include the immunogenic fragment of Msp of *Treponema denticola* with SEQ ID NO: 2 and an adjuvant. In an exemplary embodiment, the peptide vaccine may include the immunogenic fragment with a concentration between about 50 μg/ml and about 200 μg/ml. In an exemplary embodiment, the peptide vaccine may further include a pharmaceutically acceptable carrier.

Other exemplary systems, methods, features, and advantages of the implementations will be or will become, apparent to one of ordinary skill in the art upon examination of the following figures and detailed description. It is intended that all such additional systems, methods, features, and advantages be included within this description and this summary, be within the scope of the implementations and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
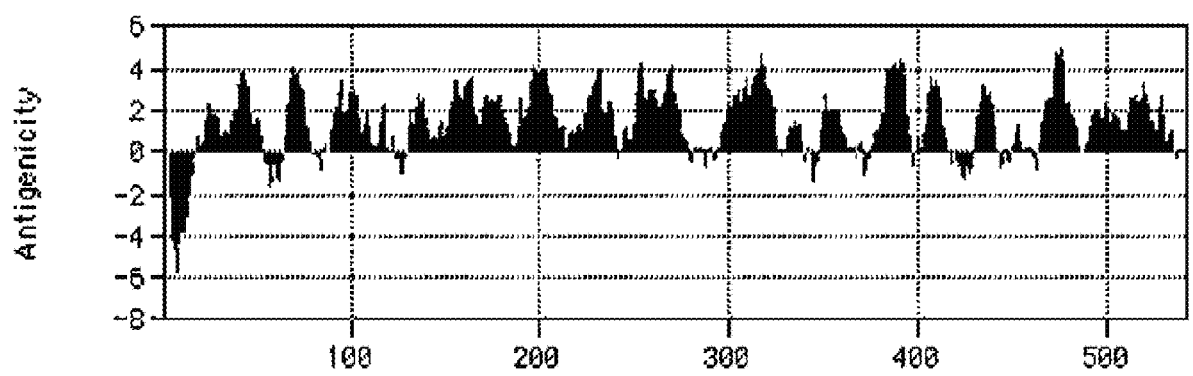
FIG. 1 shows an antigenicity profile of the Msp protein of *T. denticola*, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

The major outer sheath protein (Msp) of *T. denticola* may facilitate adhesion of *T. denticola* to mucosal surfaces and mediate pathogenesis in periodontitis. Although patients may have antibodies against Msp of *T. denticola*, these antibodies may not be produced at an enough level at the early stages of the disease; therefore, antibody production may be overtaken by bacterial growth, therefore, pathogenic effects of *T. denticola* may not be inhibited. Moreover, the presence of antibodies against the Msp may improve opsonizing effects on phagocytosis of *T. denticola* by macrophages. Therefore, stimulation of antibody production against the Msp by administering effective vaccine candidates may be useful in eliciting protective immunity in further periodontal animal models or future clinical studies.

While all parts of Msp of *T. denticola* are not immunogenic, the present disclosure describes exemplary short polypeptides in the Msp of *T. denticola* as a vaccine candidate which may be highly immunogenic and elicit protective antisera against *T. denticola*. Disclosed herein is an exemplary complementary DNA (cDNA) with SEQ ID NO: 1 which may encode against an immunogenic Msp fragment of *T. denticola*.

The present disclosure also describes exemplary prophylactic vaccine candidates to confer humoral immunity against the immunogenic Msp fragment of *T. denticola* to a subject. In an exemplary embodiment, prophylactic vaccines may be used to reduce the likelihood of a subject acquiring periodontitis. In an exemplary embodiment, the exemplary prophylactic vaccine candidates may include an exemplary DNA vaccine or an exemplary peptide vaccine.

In an exemplary embodiment, the exemplary DNA vaccine may include an exemplary complementary DNA (cDNA) of SEQ ID NO: 1 which may encode an immunogenic Msp fragment of *T. denticola*. In an exemplary embodiment, the exemplary cDNA may encode highly immunogenic Msp fragment of *T. denticola* including epitopes that trigger protective humoral immunity against *T. denticola*. In an exemplary embodiment, the exemplary cDNA may further include a nucleotide sequence of a histidine tag (His-tag).

In an exemplary embodiment, the exemplary peptide vaccine may include an immunogenic Msp fragment of *T. denticola* with SEQ ID NO: 2. In an exemplary embodiment, the exemplary peptide vaccine may include the immunogenic Msp fragment of *T. denticola* with a concentration between about 50 µg/ml and about 200 µg/ml. In an exemplary embodiment, the immunogenic Msp fragment of *T. denticola* may have a molecular weight of about 9722 Daltons. In an exemplary embodiment, the immunogenic Msp fragment of *T. denticola* may have an isoelectric point (pI) of about 9.19.

In an exemplary embodiment, the exemplary prophylactic vaccine candidate may further include an adjuvant. In an exemplary embodiment, the adjuvant may include at least one of a cytokine, a lymphokine, and a chemokine. In an exemplary embodiment, the chemokine may further include interleukin-2 (IL-2), granulocyte-macrophage-colony-stimulating factor (GM-CSF), interleukin-12 (IL-12), γ-interferon, IP-10, MIP1β, and chemokine ligand 5 (CCL5). In an exemplary embodiment, the exemplary prophylactic vaccine candidate may include Freund's adjuvant. In an exemplary embodiment, the exemplary peptide vaccine may include the immunogenic Msp fragment of *T. denticola* and the Freund's adjuvant with a volume ratio of about 1:1.

As used herein, "adjuvant" refers to one or more substances that cause stimulation of the immune system. In this context, an adjuvant may be used to enhance an immune response to one or more vaccine antigens or antibodies. An adjuvant may be administered to a subject before, in combination with, or after administration of the vaccine. Examples of chemical compounds used as adjuvants may include at least one of aluminum compounds, oils, block polymers, immune-stimulating complexes, vitamins and minerals (e.g., vitamin E, vitamin A, selenium, and vitamin B12), saponins, and bacterial and fungal cell wall components.

In an exemplary implementation, the present disclosure further describes an exemplary method for vaccination against periodontitis. In an exemplary embodiment, the exemplary method may include administering the exemplary DNA vaccine with SEQ ID NO: 1 or the exemplary peptide vaccine with SEQ ID NO: 2 to a subject. In an exemplary embodiment, the immunogenic Msp fragment of *T. denticola* with SEQ ID NO: 2 may carry epitopes that trigger protective humoral immunity against *T. denticola*.

In an exemplary embodiment, the DNA vaccine and the peptide vaccine may further include a pharmaceutically acceptable carrier. The term "pharmaceutically acceptable carrier" refers to a carrier medium that does not interfere with the effectiveness of the biological activity of the DNA vaccine and the peptide vaccine and is not toxic to the subject to whom it is administered. In an exemplary embodiment, the exemplary DNA vaccine or the exemplary peptide vaccine may be administered intravenously, intramuscularly, subcutaneously, intraperitoneally, intranasally, intracerebroventricularly, intrathecally, or as an aerosol for vaccination against periodontitis.

In an exemplary embodiment, administering the exemplary DNA vaccine or the exemplary peptide vaccine to a subject may trigger protective humoral immunity against *T. denticola* by producing antiserum against the exemplary immunogenic Msp fragment of *T. denticola* with SEQ ID NO: 2. In an exemplary embodiment, antiserum against the SEQ ID NO: 2 may significantly inhibit attachment of *T. denticola* to human fibronectin and human gingival fibroblasts (HGFs).

In an exemplary embodiment, antiserum against the SEQ ID NO: 2 may inhibit detachment of HGFs from substratum upon exposure to *T. denticola*. In an exemplary embodiment, considering the complexity and polymicrobial nature of periodontitis, the exemplary DNA vaccine or the exemplary peptide vaccine may be used individually or as a component of a possible multivalent periodontal vaccine.

EXAMPLES

Example 1

Antigenicity Profile of Msp Protein of *T. denticola*

In this example, to find out the amino acid motifs that may have a high probability of epitope activity, antigenicity profile of Msp was determined using the MacVector program. Antigenicity profile is a computational calculation of a protein sequence that may predict and may locate possible exposed surface peaks of the protein, such as peaks that might be antigenic sites, based on knowledge of which amino acids are more likely to be found in surface domains of proteins of a known structure. The MacVector program takes a frame of 11 amino acids and sums the eleven fractional probabilities of the amino acids in the window and divides by eleven to yield a running average of the fractional antigenicity index along the length of the protein. Image analysis was performed on the antigenicity profile of the Msp protein.

FIG. 1 shows an antigenicity profile of the Msp protein of *T. denticola*, consistent with one or more exemplary embodiments of the present disclosure. Referring to FIG. 1, regions that plot above the horizontal axis are predicted to be exposed at the Msp surface. Also, surface areas of antigenicity peaks were measured using ImageJ software and reported in arbitrary units (A.U.) in TABLE. 1. Referring to FIG. 1 and TABLE. 1, the F3 fragment (amino acids 174-282) was located on a highly antigenic region along with the antigenicity plot and constituted a major antigenic region among the six fragments.

TABLE 1

Antigenicity profile of Msp protein of *T. denticola*

| Msp fragment | Amino acid sequence | Antigenicity (A.U.) |
|---|---|---|
| F1 | 20-108 | 691 |
| F2 | 87-195 | 1536 |
| F3 | 174-282 | 2310 |
| F4 | 261-384 | 1318 |
| F5 | 369-456 | 1062 |
| F6 | 435-543 | 1722 |

Example 2

Production of Different Msp Fragments of *T. denticola*

In this example, six fragments of the Msp protein of *T. denticola* were produced as follows. At first, the nucleotide sequences of all fragments were cloned into pET16b plasmids and transformed into the expression host *E. coli* BL21. Recombinant plasmids were screened by colony-PCR, and all constructs were sequenced to confirm authenticity.

In the next step, recombinant His-tagged polypeptides were expressed as follows. *E. coli* BL21 containing either plasmid constructs or no pET16b (as control) were incubated at 37° C. with shaking in 100 ml of LB medium containing 100 mg/ml ampicillin at $OD_{600}$=0.7. Then, the expression was induced by adding about 0.5 mM isopropyl β-D-thiogalactopyranoside (IPTG), and the cultures were incubated for a further 18 hours at a temperature of about 25° C. Bacteria were harvested by centrifugation and lysed. After that, a solution containing guanidine hydrochloride (6 M), $NaH_2PO_4$ (100 mM), and Tris-HCl (10 mM) was used for solubilizing the bacteria. After that, the solubilized mixture was sonicated on ice for 5×30 second pulses interspersed with 30 seconds of rest.

In the next step, column purification and refolding of recombinant His-tagged Msp fragments were done as follows. Cellular debris was cleared by centrifugation, and the supernatant containing His-tagged polypeptides was applied to Ni-NTA column which had been equilibrated with 100 mM $NaH_2PO_4$, 10 mM Tris-HCl and 20 mM imidazole pH 7.4 and incubated for 1 h. Washing was performed using the same buffer with a linear 20-100 mM imidazole gradient. Recombinant polypeptides were eluted with the same buffer including 500 mM imidazole. Refolding of polypeptides was performed by dialysis at 4° C. against 7 M urea and 50 mM Tris-HCl at a pH level of 7.4 with four buffer changes. Urea concentration was gradually decreased till reaching the final refolding buffer containing 50 mM Tris-HCl.

After that, the produced recombinant fragments of Msp protein were visualized using sodium dodecyl sulfate-polyacrylamide gel electrophoresis (SDS-PAGE) according to the method of Laemmli using 12% cross-linked polyacrylamide gel. Then, unpurified and purified fractions were loaded onto the gel and molecular weight was determined using a molecular weight marker. The protein bands were visualized on the gel by Coomassie brilliant blue G-250.

Figure 2A:
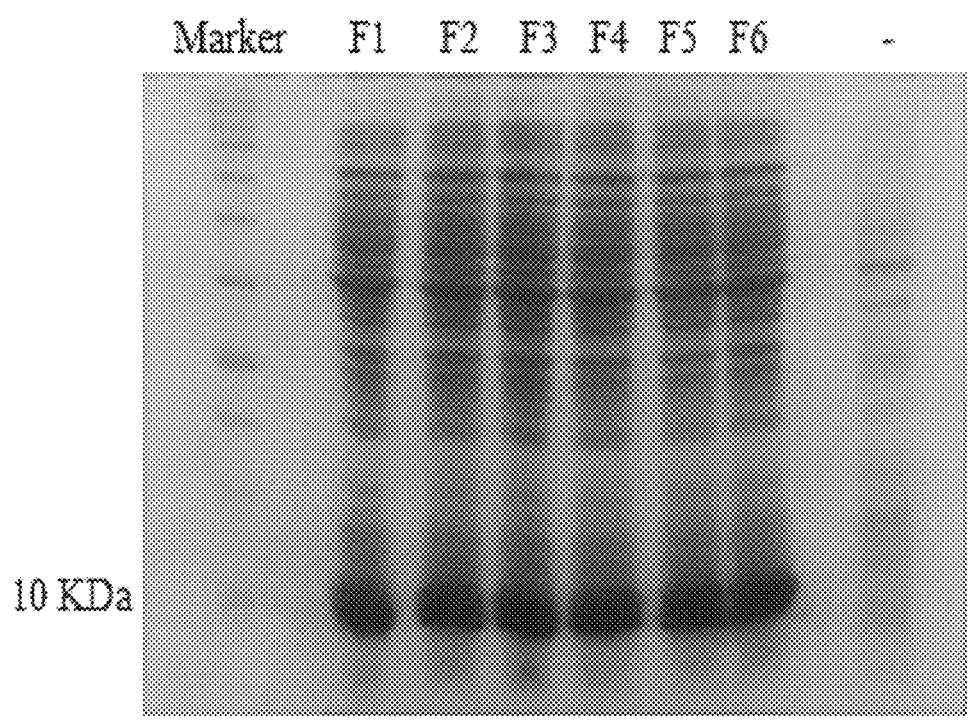
FIG. 2A shows an SDS-PAGE profile of expressed recombinant Msp fragments before purification, consistent with one or more exemplary embodiments of the present disclosure.
Figure 2B:
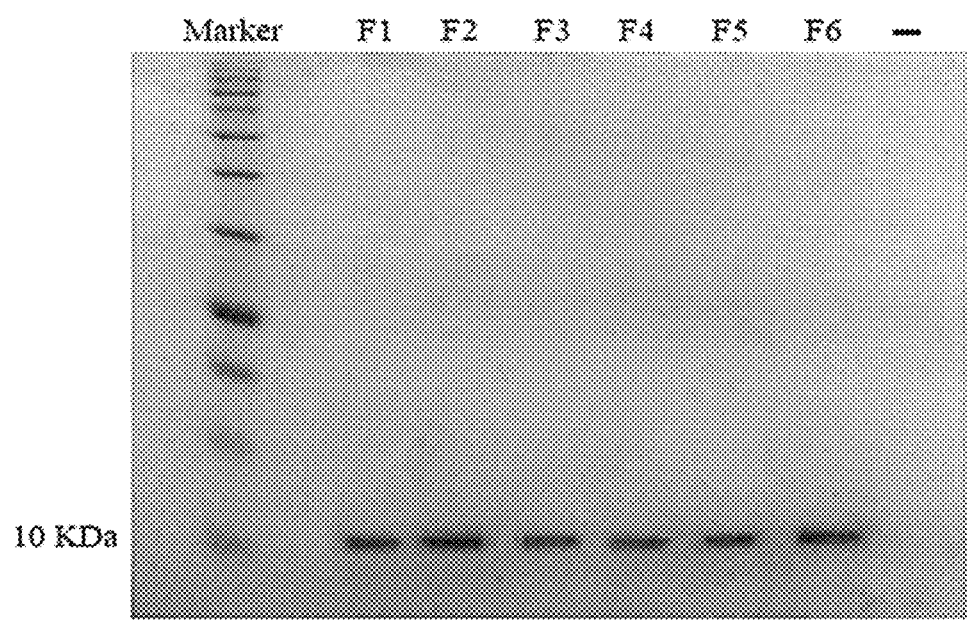
FIG. 2B shows an SDS-PAGE profile of purified recombinant Msp fragments using the Ni-NTA column, consistent with one or more exemplary embodiments of the present disclosure.

FIG. 2A shows an SDS-PAGE profile of expressed recombinant Msp fragments before purification, consistent with one or more exemplary embodiments of the present disclosure. FIG. 2B shows an SDS-PAGE profile of purified recombinant Msp fragments using the Ni-NTA column, consistent with one or more exemplary embodiments of the present disclosure. Referring to FIGS. 2A-2B, the recombinant Msp fragments with a molecular weight of about 10 kDa were visualized on the SDS-PAGE gel.

Example 3

Analysis of Antisera Against Different Msp Fragments of *T. denticola*

In this example, the presence of antisera against different Msp fragments of *T. denticola* was assessed using western blot analysis of patients' samples. Patients with severe periodontitis were recruited randomly. Peripheral blood samples were collected and drawn into a vacutainer tube containing a clot activator. Blood samples were left at room temperature for 30 min. The clots were removed by centrifugation at 2000×g at 4° C. for 10 min and the sera were collected.

For immunoblotting, different Msp fragments of *T. denticola* produced as described in EXAMPLE. 2 were transferred to polyvinylidene difluoride (PVDF) membranes. The membranes were blocked with 5% bovine serum albumin (BSA) in PBS for 3 hours. The membrane was washed using 0.05% Tween 20 in PBS and pure PBS for two times. Blots were incubated with patients' sera (diluted 1:100) for 16 hours at a temperature of 4° C. After that, binding was detected with goat horseradish peroxidase (HRP)-conjugated anti-rabbit (diluted 1:80000) with enhanced chemiluminescence (ECL) detection system. The band intensity was quantified by ImageJ software.

Figure 3:
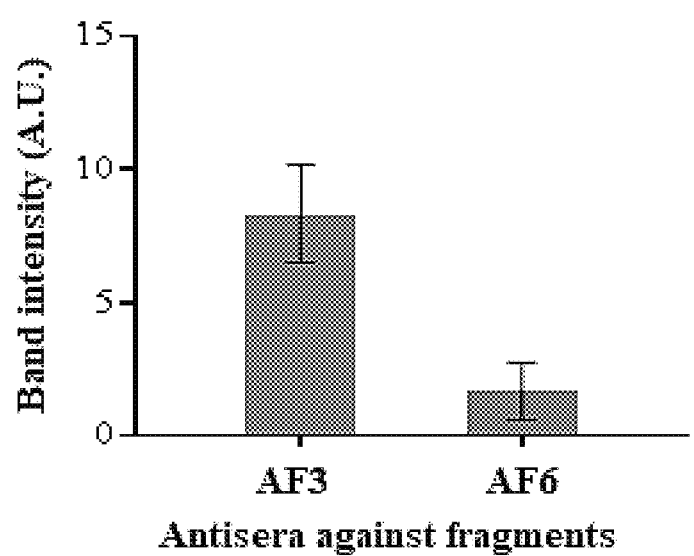
FIG. 3 shows band intensities of antisera against different Msp fragments of *T. denticola* in western blot analysis of patients' sera, consistent with one or more exemplary embodiments of the present disclosure.

FIG. 3 shows band intensities of antisera AF3 and AF6 against F3 and F6 Msp fragments of *T. denticola* in western blot analysis of patients' sera, consistent with one or more exemplary embodiments of the present disclosure. Referring to FIG. 3, antiserum AF3 against the F3 fragment (amino acids 174-282) (SEQ ID NO: 2) was detected in all 12 patient serum samples, while only four patient serum samples contained antiserum AF6 against the F6 fragment and no antiserum against the other fragments was detected in patients' samples. Therefore, according to band densities, peak heights, and peak intensities, the antiserum AF3 against the F3 fragment (SEQ ID NO: 2) was significantly higher than the antisera against the other fragments in the patient samples.

Example 4

Immunization Against Different Msp Fragments of *T. denticola*

In this example, the immunogenicity of different Msp fragments of *T. denticola* was examined using New Zealand white rabbits. It is well-established that suitable preclinical studies before starting a clinical trial in humans are pivotal to obtain high quality data and to select effective vaccine candidate in clinical care. Major goals of preclinical tests in selecting vaccine candidates are measuring titers of antisera against different vaccine candidates which may be performed on animals. Animal experiments especially immunological studies on rabbits have a long history in the field of vaccine research.

At first, six male New Zealand white rabbits were immunized by subcutaneously injecting 1 ml of each Msp fragments of *T. denticola* (150 µg, in 50 mM Tris buffer at a pH level of 7.4) mixed with an equal volume of Freund complete adjuvant. The animals were pre-bled on day 0 as a rabbit pre-immune serum. Subsequent booster injections of the same amount of each Msp fragments of *T. denticola* with incomplete Freund adjuvant were performed after 15 and 45 days. The rabbits were bled via cardiac puncture one week after the last booster. The sera were obtained and stored at a temperature of about −20° C.

Antiserum titers of each Msp fragment of *T. denticola* were determined by enzyme-linked immunosorbent assay (ELISA). The rabbit antisera against different Msp fragments of *T. denticola* and the rabbit pre-immune serum were used in ELISA for detecting the most immunogenic Msp fragment of *T. denticola*. At first, 96-well plates were coated with each Msp fragment of *T. denticola* in PBS at a temperature of 4° C. for 16 hours. Each Msp fragment of *T. denticola* had a concentration of about 20 µg/ml. The plates were washed twice with 0.05% Tween 20 in PBS and once with PBS, and the wells were blocked with 1% (w/v) bovine serum albumin (BSA) for 2 hours and then washed.

After that, serial dilutions of antisera (1:500 to 1:16384000) were added to the wells and incubated at a temperature of 37° C. for 1 hour, and washed as explained above. Secondary goat HRP-conjugated anti-rabbit (diluted 1:10000 in PBS) was added to wells and incubated for 1 hour. The wells were washed and tetramethylbenzidine (TMB) was added to them. Finally, stop solution (1 N $H_2SO_4$) was added to each well. Optical absorbance was read at a wavelength of about 450 nm. The experiments were performed for antisera against different Msp fragments of *T. denticola* and the rabbit pre-immune serum at least three times.

TABLE. 2 represents titers of antisera against different Msp fragments of *T. denticola*. Referring to TABLE. 2, F3 fragment elicited the highest antiserum titer compared to the other fragments. Therefore, the F3 fragment was the most immunogenic while fragment 1 (F1) immunized the rabbits very weakly.

TABLE 2

Antiserum titers against different Msp fragments of *T. denticola*

| Msp fragment of *T. denticola* | Antiserum Titer |
|---|---|
| F1 | $5 \times 10^2$ |
| F2 | $8 \times 10^3$ |
| F3 | $1 \times 10^7$ |
| F4 | $4 \times 10^3$ |
| F5 | $8 \times 10^3$ |
| F6 | $1 \times 10^4$ |

Example 5

Adhesion Inhibition Assay of Different Msp Fragments of *T. denticola*

The Msp protein of *T. denticola* functions as a porin, perturbs calcium signaling in human gingival fibroblasts (HGFs) and plays a key role in co-aggregation of *T. denticola* with other bacteria. Also, the Msp protein mediates adhesion of *T. denticola* to host extracellular matrix proteins such as fibronectin and host fibroblasts. Therefore, candidate vaccines for periodontitis may effectively raise antibodies that inhibit attachment of *T. denticola* to plasma fibronectin and fibroblast cells. In this example, the effects of antisera against different Msp fragments of *T. denticola* on the attachment of *T. denticola* bacteria to human plasma fibronectin and HGFs were assessed.

At first, *T. denticola* bacteria were biotinylated as follows. Late-exponential-phase *T. denticola* cells were harvested by centrifugation, washed three times in ice-cold phosphate-buffered saline (PBS) and suspended in ice-cold PBS at an optical density ($OD_{600}$) of 0.1 ($4.2 \times 10^8$ cells/ml). Then, EZ-Link sulfo-NHS-LC-biotin reagent at a concentration of about 1 mg/ml was added to the cell suspensions, and the suspensions were incubated for 30 minutes at room temperature. Excess biotin was removed by three rounds of sequential centrifugation and washing of the cells in ice-cold PBS, and suspensions were readjusted to an $OD_{600}$ of 0.1 and stored on ice for the adhesion inhibition assay.

After that, different dilutions of antisera against the Msp fragments of *T. denticola* (1:10, 1:100, 1:1000, and 1:10000) were incubated with the biotinylated *T. denticola* in PBS at a temperature of about 37° C. for 1 hour with gentle agitation. Two washes in PBS by centrifuging at a speed of about 9,000×g for 20 minutes were used to remove unbound antibodies. The biotinylated *T. denticola* bound to antibodies were used for the adhesion assay. Biotinylated *T. denticola* bacteria were incubated with rabbit pre-immune serum as a control group. Also, PBS and biotinylated *T. denticola* alone were used as negative control groups.

In the next step, fibronectin adhesion assay was done by adding human plasma fibronectin to 96-well plastic plates with an amount of about 0.5 mg per well and incubated at a temperature of about 4° C. for 16 hours. Non-specific binding sites in coated wells were blocked with 1% (w/v) bovine serum albumin (BSA) in PBS for 1 hour at a temperature of about 22° C. Wells were also washed twice with PBSTB (PBS containing 0.1% v/v tween 20 and 0.1% w/v BSA) and once with PBS.

After that, the mixture of *T. denticola* ($1 \times 10^9$) and antisera against each Msp fragment of *T. denticola* with a dilution factor of 1:10000 and the mixture of *T. denticola* and the rabbit pre-immune serum with a dilution factor of 1:10000 were applied in triplicate wells and incubated at a temperature of about 22° C. for 2 hours. Unbound cell suspensions were removed by aspiration and wells were washed twice with PBS.

Horseradish-peroxidase-conjugated streptavidin (0.1 µg/ml) diluted in PBSTB was added to each well and incubated at a temperature of 37° C. for 1 hour. The wells were washed once in PBSTB and twice with PBS and tetramethylbenzidine (TMB) was added to them. Finally, stop solution (1 N $H_2SO_4$) was added to each well. Optical absorbance was read at a wavelength of about 450 nm. The experiment was repeated at least three times and the results are presented in TABLE. 3. The optical densities of each sample were subtracted from its control and expressed as a percentage of inhibition compared to the rabbit pre-immune serum to normalize the data. The values represent the mean±standard deviation of three independent experiments using samples in triplicate. Each group of AF1-AF6 refers to an antiserum against F1-F6 Msp fragments of *T. denticola*. For example, AF1 refers for antiserum against the F1 fragment Msp fragment of *T. denticola*.

TABLE 3

Effect of rabbit antisera against Msp fragment of *T. denticola* on the attachment of *T. denticola* to human fibronectin. AF1-AF6: antisera against Msp fragments F1-F6

| Antisera | % inhibition of attachment |
| --- | --- |
| AF1 | 4 ± 0.131 |
| AF2 | 7 ± 0.096 |
| AF3 | 63 ± 0.046 |
| AF4 | 21 ± 0.100 |
| AF5 | 15 ± 0.115 |
| AF6 | 7 ± 0.157 |

Referring to TABLE. 3, the data show that antiserum against fragment 3 (AF3) significantly ($p<0.05$) blocked the binding of *T. denticola* to fibronectin (63% inhibition). While adhesion inhibition of *T. denticola* to fibronectin upon treatment with antisera of other fragments was not more than 21%, AF3 which is an antiserum against F3 fragment (SEQ ID NO: 2) shows a 3-fold inhibition of *T. denticola* attachment.

Moreover, a fibroblast adhesion assay was done to evaluate the effect of antisera against different Msp fragments of *T. denticola* on the attachment of *T. denticola* to fibroblast cells. At first, human gingival fibroblasts (HGFs) with a seeding density of about $2 \times 10^4$ fibroblast cells/ml were plated in a 96-well plate to grow 48 hours and reach confluency between 90% and 95%. The number of *T. denticola* used in this assay ($10^6$) was the threshold of fibroblast detachment from substratum upon exposure to the bacteria. This helps measure inhibition more accurately and prevents the disruptive effect of fibroblast detachment.

The wells were washed two times with PBS to remove detached cells. The mixture of *T. denticola* ($10^6$ biotinylated bacteria) and antisera against different Msp fragments of *T. denticola* (diluted 1:1000) and a mixture of *T. denticola* ($10^6$ biotinylated bacteria) and the rabbit pre-immune serum (diluted 1:1000) were added in triplicate wells and incubated for 2 hours at 37° C. and 5% $CO_2$. Unbound *T. denticola* bacteria were removed by aspiration.

The detection was performed using horseradish-peroxidase-conjugated streptavidin as done in fibronectin adhesion assay. The experiments were performed for antisera against all Msp fragments of *T. denticola* and rabbit pre-immune serum three times. TABLE. 4 represents results of fibroblast adhesion assay in the presence of rabbit antisera against different Msp fragments of *T. denticola*. The optical densities of the serum samples were subtracted from their controls and expressed as a percentage of inhibition compared to rabbit pre-immune serum to normalize the data. The values represent the mean±standard deviation of three independent experiments using samples in triplicate. Each group of AF1-AF6 refers to an antiserum against F1-F6 Msp fragments of *T. denticola*. For example, AF1 refers for antiserum against the F1 fragment Msp fragment of *T. denticola*.

TABLE 4

Effect of antisera against different Msp fragments of *T. denticola* on the attachment of *T. denticola* to HGF cells. AF1-AF6: antisera against Msp fragments F1-F6

| Antisera | % Inhibition of Attachment |
| --- | --- |
| AF1 | −25 ± 0.071 |
| AF2 | −7 ± 0.078 |
| AF3 | 29 ± 0.046 |
| AF4 | 2 ± 0.109 |
| AF5 | 6 ± 0.054 |
| AF6 | −8 ± 0.081 |

Referring to TABLE. 4, antiserum AF3 against F3 fragment (SEQ ID NO: 2) significantly blocked binding of *T. denticola* to fibroblasts (30%) and had inhibitory effects at least 23 times more than antisera against other Msp fragments of *T. denticola*.

Example 6

Inhibition of Cell Detachment in the Presence of Antisera Against Different Msp Fragments of *T. denticola*

In this example, cell detachment assay was performed in the presence of antisera against different Msp fragments of *T. denticola*. At first, about $2 \times 10^5$ HGF cells were seeded in each well of a 24-well plate to grow overnight to obtain a monolayer. The wells were washed two times with warm PBS to remove detached cells. Then the monolayers were exposed to different concentrations of *T. denticola* ($10^8$ and $10^9$ bacteria) mixed with either antiserum against each Msp fragment of *T. denticola* (diluted 1:20) or rabbit pre-immune serum (diluted 1:20) in triplicate wells.

The plates were incubated for 2 hours at a temperature of about 37° C. in a 5% $CO_2$ incubator. After that, supernatants were removed by aspiration and remaining adherent cells were trypsinized and the number of attached cells was counted with a Coulter counter. Control wells consisted of the HGFs exposed to α-MEM medium without antiserum. The experiments were repeated four times.

Figure 4:
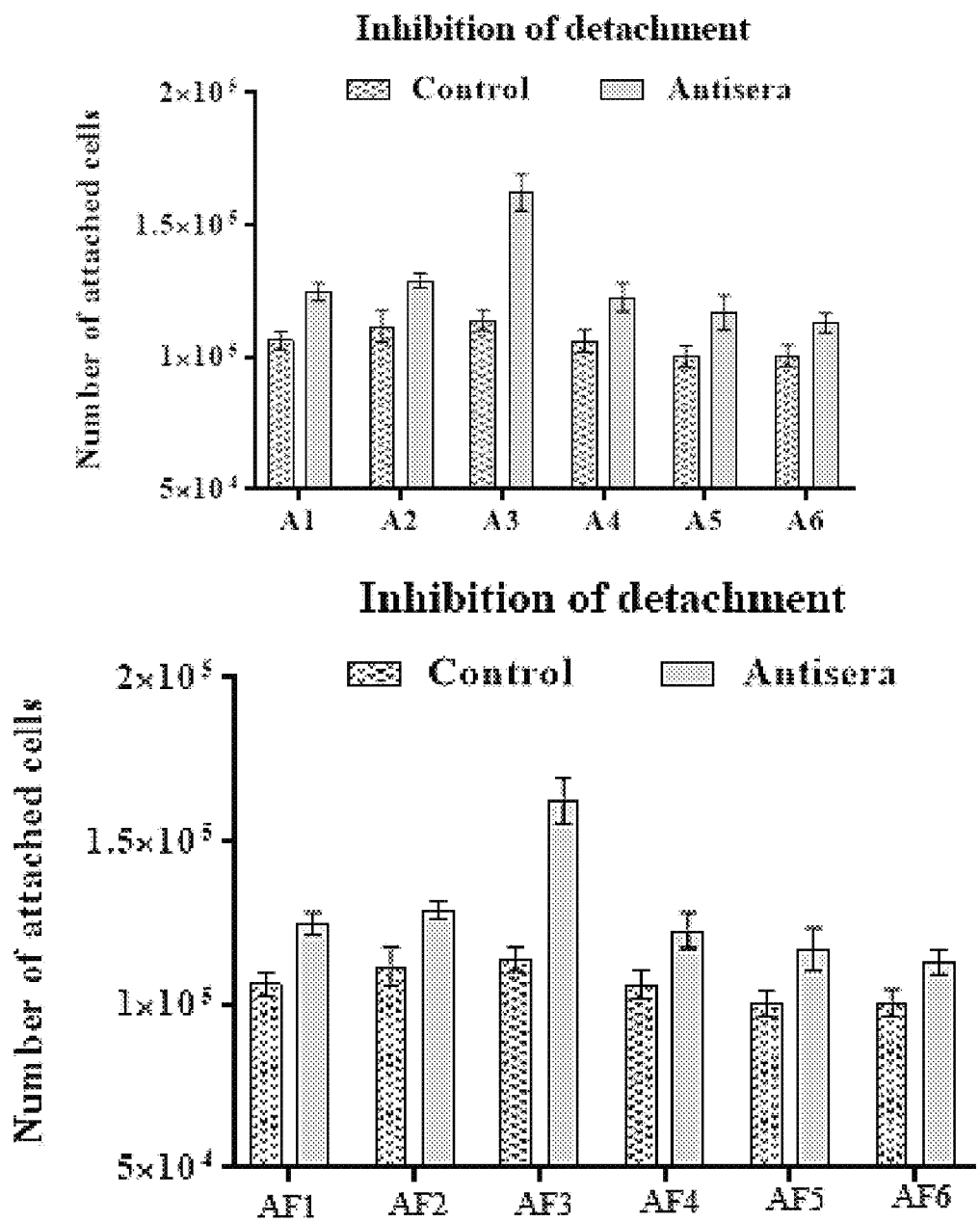
FIG. 4 shows a number of attached human gingival fibroblasts (HGFs) after exposure to *T. denticola* bacteria in the presence of antisera against different Msp fragments of *T. denticola*, consistent with one or more exemplary embodiments of the present disclosure.

FIG. 4 shows the number of attached HGF cells after exposure to *T. denticola* bacteria in the presence of antisera against different Msp fragments of *T. denticola*, consistent with one or more exemplary embodiments of the present disclosure. Each group of AF1-AF6 refers to an antiserum against F1-F6 Msp fragments of *T. denticola*. For example, AF1 refers for antiserum against the F1 fragment Msp fragment of *T. denticola*. Referring to FIG. 4, antiserum AF3 against the F3 fragment (SEQ ID NO: 2) significantly inhibits cell detachment in comparison with other groups. TABLE. 5 shows the percentage inhibition of HGFs detachment using antisera (AF1-AF6) against different Msp fragments of *T. denticola*. The number of HGF upon exposure to serum samples were subtracted from their controls and expressed as inhibition percentage of cell detachment for normalizing the data.

TABLE 5

Inhibition of HGFs detachment by *T. denticola* using antisera against different Msp fragments of *T. denticola*. AF1-AF6: antisera against fragments F1-F6

| Antisera | % Inhibition of cell detachment |
|---|---|
| AF1 | 17 ± 9 |
| AF2 | 15 ± 12 |
| AF3 | 42 ± 11 |
| AF4 | 15 ± 10 |
| AF5 | 16 ± 6 |
| AF6 | 12 ± 9 |

Referring to TABLE. 5, the data show that all six antisera inhibit the detachment of HGFs to some extent. However, antiserum against F3 fragment (SEQ ID NO: 2) protected the HGFs form detachment two times as much as other antisera upon exposure to *T. denticola*. Antiserum against F3 fragment (SEQ ID NO: 2) protected 42% of the HGFs from detachment while the other antisera protected only 12-17% of the cells from detachment.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such away. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A complementary DNA (cDNA), wherein the cDNA consisting of SEQ ID NO: 1 and encodes an immunogenic fragment with a molecular weight of 9722 Daltons of major outer sheath protein (Msp) of *Treponema denticola*.

2. The cDNA of claim 1, wherein the cDNA encodes the immunogenic fragment with an isoelectric point of 9.19.

3. The cDNA of claim 1, wherein the cDNA further comprises a nucleotide sequence of a histidine tag (His-tag).

* * * * *

SEQUENCE LISTING

```
<160> NUMBER OF SEQ ID NOS: 2

<210> SEQ ID NO 1
<211> LENGTH: 297
```

```
<212> TYPE: DNA
<213> ORGANISM: Treponema denticola

<400> SEQUENCE: 1
ggtctgaaat tcggttctaa cggttcttgg aaagcgaaag gtaccaccgc gcaggacaaa      60
ttcaaagttg ttgacctgaa agttggtgac accctgatcg cgggtgcgac ctactacaaa     120
cagaacggta tcgacgcgga aggtaaaccg atcttctctt ctacggcagc ggttttcgcc     180
gcacctccga ccgttggtgc gggtgaagac ggcaaatacc tggttaagac cgcgtctacc     240
gcgacgggtc cggctgcgaa caaatacgcg ttcggtctgg actaataata aggatcc       297

<210> SEQ ID NO 2
<211> LENGTH: 94
<212> TYPE: PRT
<213> ORGANISM: Treponema denticola

<400> SEQUENCE: 2

Gly Leu Lys Phe Gly Ser Asn Gly Ser Trp Lys Ala Lys Gly Thr Thr
1               5                   10                  15

Ala Gln Asp Lys Phe Lys Val Val Asp Leu Lys Val Gly Asp Thr Leu
            20                  25                  30

Ile Ala Gly Ala Thr Tyr Tyr Lys Gln Asn Gly Ile Asp Ala Glu Gly
        35                  40                  45

Lys Pro Ile Phe Ser Ser Thr Ala Ala Val Phe Ala Ala Pro Pro Thr
    50                  55                  60

Val Gly Ala Gly Glu Asp Gly Lys Tyr Leu Val Lys Thr Ala Ser Thr
65                  70                  75                  80

Ala Thr Gly Pro Ala Ala Asn Lys Tyr Ala Phe Gly Leu Asp
                85                  90
```